(12) United States Patent
Hill et al.

(10) Patent No.: US 12,387,839 B2
(45) Date of Patent: Aug. 12, 2025

(54) METHOD AND SYSTEM FOR LABELING MEDICAL IMAGES

(71) Applicant: Northwestern University, Evanston, IL (US)

(72) Inventors: Virginia Boyce Hill, Chicago, IL (US); Michael Alexander Iorga, Chicago, IL (US); Aggelos K. Katsaggelos, Chicago, IL (US); Todd B. Parrish, Chicago, IL (US)

(73) Assignee: Northwestern University, Evanston, IL (US)

( * ) Notice: Subject to any disclaimer, the term of this patent is extended or adjusted under 35 U.S.C. 154(b) by 311 days.

(21) Appl. No.: 17/943,390

(22) Filed: Sep. 13, 2022

(65) Prior Publication Data

US 2023/0078011 A1    Mar. 16, 2023

Related U.S. Application Data

(60) Provisional application No. 63/243,373, filed on Sep. 13, 2021.

(51) Int. Cl.
*G16H 30/40* (2018.01)
*G06F 40/40* (2020.01)
(Continued)

(52) U.S. Cl.
CPC ............ *G16H 30/40* (2018.01); *G06F 40/40* (2020.01); *G06T 7/0012* (2013.01); *G16H 30/20* (2018.01);
(Continued)

(58) Field of Classification Search
CPC ........ G16H 30/40; G06H 30/20; G06F 40/40; G06T 7/0012; G06T 2207/10081; G06T 2207/20081
See application file for complete search history.

(56) References Cited

U.S. PATENT DOCUMENTS

| 2018/0310828 A1* | 11/2018 | DiMaio | A61B 5/0075 |
| 2019/0082998 A1* | 3/2019 | Nowroozi | A61B 5/0507 |
| 2020/0075148 A1* | 3/2020 | Nguyen | G16H 20/10 |

FOREIGN PATENT DOCUMENTS

| CN | 110287870 A | * | 9/2019 | ... G06T 2207/20081 |
| CN | 118355447 A | * | 7/2024 | ........ C12Q 1/6886 |
| JP | 2020522690 A | * | 7/2020 | ........ G16H 30/40 |
| WO | WO-2021243246 A1 | * | 12/2021 | ........ G16H 50/20 |
| WO | WO-2022015597 A1 | * | 1/2022 | ........ A61B 5/0075 |

OTHER PUBLICATIONS

O'Connor SD, Bhalla M. Should Artificial Intelligence Tell Radiologists Which Study to Read Next? *Radiology: Artificial Intelligence.* Mar. 1, 2021;3(2):e210009.
(Continued)

*Primary Examiner* — Mohammad K Islam
(74) *Attorney, Agent, or Firm* — Bell & Manning, LLC (57) ABSTRACT

A system for automatically labeling massive quantities of image report data includes a memory configured to store image data and metadata corresponding to the image data. The system also includes a processor operatively coupled to the memory and configured to apply a natural language processing algorithm to identify one or more characteristics of the image report data and the metadata. The processor is also configured to label the image report data based at least in part on the one or more identified characteristics to form a labeled dataset.

18 Claims, 12 Drawing Sheets

| Imaging Finding | Class | Count |
|---|---|---|
| Epidural Hemorrhage | Hemorrhage | 7 |
| Subdural Hemorrhage | Hemorrhage | 71 |
| Subarachnoid Hemorrhage | Hemorrhage | 73 |
| Intraventricular Hemorrhage | Hemorrhage | 57 |
| Intra-axial or Parenchymal Hemorrhage | Hemorrhage | 96 |
| Post-surgical Hemorrhage | Hemorrhage | 62 |
| Arterial Ischemic Infarct | Infarct | 65 |
| Hyperdense Artery | Infarct | 4 |
| Acute Venous Infarct | Infarct | 1 |
| Dural Venous Sinus Thrombosis | Other | 0 |
| Subdural Fluid Collection | Other | 43 |
| Subfalcine Herniation or Midline Shift | Herniation | 73 |
| Transtentorial Herniation | Herniation | 2 |
| Tonsillar Herniation | Herniation | 2 |
| Uncal Herniation | Herniation | 7 |
| Craniotomy or Craniectomy | Postsurgical | 12 |
| Upward Herniation | Herniation | 1 |
| Significant Mass Effect or Effacement | Mass Effect | 73 |
| Small Mass Effect or Effacement | Mass Effect | 90 |
| Ventricular Entrapment | Other | 5 |
| Postsurgical Image | Postsurgical | 227 |
| Chronic Fracture | Other | 14 |
| Old Aneurysm or Arteriovenous Malformation | Other | 48 |
| Intracranial Hypotension | Other | 0 |

| Imaging Finding (Cont'd) | Class (Cont'd) | Count (Cont'd) |
|---|---|---|
| Arachnoid Cyst | Other | 12 |
| Other Chronic Condition | Other | 255 |
| Hemorrhagic Transformation of Infarct | Hemorrhage | 8 |
| Hydrocephalus | Hydrocephalus | 58 |
| Abscess | Other | 3 |
| Meningitis | Other | 1 |
| Ventriculitis | Other | 0 |
| Encephalitis | Other | 1 |
| Parenchymal Tumor | Tumor | 14 |
| Extra-axial Tumor | Tumor | 26 |
| Osseous Tumor | Tumor | 15 |
| Metastasis | Tumor | 11 |
| Orbital Mass | Tumor | 3 |
| Skull Base Lysis | Other | 2 |
| White Matter Disease | Other | 2 |
| Acute Orbital Pathology | Other | 15 |
| Fracture | Fracture | 56 |
| Traumatic Encephalomalacia | Other | 14 |
| Vasogenic Edema | Edema | 86 |
| Cerebral Edema | Edema | 4 |
| Pneumocephalus | Pneumocephalus | 57 |
| Chronic White Matter Disease | White Matter Disease | 213 |
| Chronically Prominent Ventricles | Other | 3 |
| Volume Loss | Volume Loss | 350 |
| Wallerian Degeneration | Other | 12 |

(51) Int. Cl.
*G06T 7/00* (2017.01)
*G16H 30/20* (2018.01)

(52) U.S. Cl.
CPC .............. *G06T 2207/10081* (2013.01); *G06T 2207/20081* (2013.01)

(56) References Cited

OTHER PUBLICATIONS

O'Neill TJ, Xi Y, Stehel E, Browning T, Ng YS, Baker C, et al. Active Reprioritization of the Reading Worklist Using Artificial Intelligence Has a Beneficial Effect on the Turnaround Time for Interpretation of Head CT with Intracranial Hemorrhage. *Radiology: Artificial Intelligence*. Mar. 1, 2021;3(2): e200024.

Chilamkurthy S, Ghosh R, Tanamala S, Biviji M, Campeau NG, Venugopal VK, et al. Deep learning algorithms for detection of critical findings in head CT scans: a retrospective study. *The Lancet*. Dec. 1-7, 2018; vol. 392 (Issue 10162):2388-96.

Zech J, Pain M, Titano J, Badgeley M, Schefflein J, Su A, et al. Natural Language-based Machine Learning Models for the Annotation of Clinical Radiology Reports. *Radiology*. May 2018;287(2):570-80.

Barash Y, Guralnik G, Tau N, Soffer S, Levy T, Shimon O, et al. Comparison of deep learning models for natural language processing-based classification of non-English head CT reports. *Neuroradiology*. Oct. 2020;62(10):1247-56.

\* cited by examiner

| Imaging Finding | Class | Count |
|---|---|---|
| Epidural Hemorrhage | Hemorrhage | 7 |
| Subdural Hemorrhage | Hemorrhage | 71 |
| Subarachnoid Hemorrhage | Hemorrhage | 73 |
| Intraventricular Hemorrhage | Hemorrhage | 57 |
| Intra-axial or Parenchymal Hemorrhage | Hemorrhage | 96 |
| Post-surgical Hemorrhage | Hemorrhage | 62 |
| Arterial Ischemic Infarct | Infarct | 65 |
| Hyperdense Artery | Infarct | 4 |
| Acute Venous Infarct | Infarct | 1 |
| Dural Venous Sinus Thrombosis | Other | 0 |
| Subdural Fluid Collection | Other | 43 |
| Subfalcine Herniation or Midline Shift | Herniation | 73 |
| Transtentorial Herniation | Herniation | 2 |
| Tonsillar Herniation | Herniation | 2 |
| Uncal Herniation | Herniation | 7 |
| Craniotomy or Craniectomy | Postsurgical | 12 |
| Upward Herniation | Herniation | 1 |
| Significant Mass Effect or Effacement | Mass Effect | 73 |
| Small Mass Effect or Effacement | Mass Effect | 90 |
| Ventricular Entrapment | Other | 5 |
| Postsurgical Image | Postsurgical | 227 |
| Chronic Fracture | Other | 14 |
| Old Aneurysm or Arteriovenous Malformation | Other | 48 |
| Intracranial Hypotension | Other | 0 |

| Imaging Finding (Cont'd) | Class (Cont'd) | Count (Cont'd) |
|---|---|---|
| Arachnoid Cyst | Other | 12 |
| Other Chronic Condition | Other | 255 |
| Hemorrhagic Transformation of Infarct | Hemorrhage | 8 |
| Hydrocephalus | Hydrocephalus | 58 |
| Abscess | Other | 3 |
| Meningitis | Other | 1 |
| Ventriculitis | Other | 0 |
| Encephalitis | Other | 1 |
| Parenchymal Tumor | Tumor | 14 |
| Extra-axial Tumor | Tumor | 26 |
| Osseous Tumor | Tumor | 15 |
| Metastasis | Tumor | 11 |
| Orbital Mass | Tumor | 3 |
| Skull Base Lysis | Other | 2 |
| White Matter Disease | Other | 2 |
| Acute Orbital Pathology | Other | 15 |
| Fracture | Fracture | 56 |
| Traumatic Encephalomalacia | Other | 14 |
| Vasogenic Edema | Edema | 86 |
| Cerebral Edema | Edema | 4 |
| Pneumocephalus | Pneumocephalus | 57 |
| Chronic White Matter Disease | White Matter Disease | 213 |
| Chronically Prominent Ventricles | Other | 3 |
| Volume Loss | Volume Loss | 350 |
| Wallerian Degeneration | Other | 12 |

| Finding | ROC-AUC | Sensitivity | Specificity | Accuracy |
|---|---|---|---|---|
| Edema | 0.917 (0.905 – 0.929) | 0.856 (0.783 – 0.928) | 0.895 (0.875 – 0.915) | 0.891 (0.827 – 0.956) |
| Fracture | 0.959 (0.947 – 0.970) | 0.929 (0.861 – 0.996) | 0.887 (0.867 – 0.907) | 0.889 (0.807 – 0.971) |
| Hemorrhage | 0.980 (0.977 – 0.984) | 0.986 (0.970 – 1.00) | 0.925 (0.907 – 0.943) | 0.938 (0.906 – 0.970) |
| Herniation | 0.978 (0.971 – 0.985) | 0.961 (0.917 – 1.00) | 0.908 (0.890 – 0.927) | 0.912 (0.849 – 0.976) |
| Hydrocephalus | 0.934 (0.920 – 0.948) | 0.828 (0.730 – 0.925) | 0.905 (0.886 – 0.923) | 0.900 (0.823 – 0.977) |
| Infarct | 0.851 (0.833 – 0.870) | 0.809 (0.715 – 0.902) | 0.758 (0.731 – 0.785) | 0.761 (0.660 – 0.863) |
| Mass Effect | 0.960 (0.953 – 0.966) | 0.961 (0.930 – 0.991) | 0.855 (0.832 – 0.879) | 0.871 (0.818 – 0.925) |
| Pneumocephalus | 0.953 (0.941 – 0.965) | 0.982 (0.948 – 1.00) | 0.839 (0.816 – 0.863) | 0.847 (0.754 – 0.941) |
| Postoperative | 0.968 (0.964 – 0.973) | 0.916 (0.880 – 0.952) | 0.907 (0.887 – 0.928) | 0.909 (0.872 – 0.947) |
| Tumor | 0.873 (0.855 – 0.890) | 0.831 (0.740 – 0.922) | 0.776 (0.750 – 0.803) | 0.779 (0.679 – 0.880) |
| Volume Loss | 0.971 (0.967 – 0.974) | 0.934 (0.908 – 0.960) | 0.946 (0.929 – 0.964) | 0.942 (0.918 – 0.967) |
| White Matter | 0.919 (0.912 – 0.926) | 0.826 (0.775 – 0.877) | 0.904 (0.883 – 0.924) | 0.887 (0.845 – 0.930) |

METHOD AND SYSTEM FOR LABELING MEDICAL IMAGES

CROSS-REFERENCE TO RELATED APPLICATION

The present application claims the priority benefit of U.S. Provisional Pat. App. No. 63/243,373 filed on Sep. 13, 2021, the entire disclosure of which is incorporated herein by reference.

BACKGROUND

A computerized tomography (CT) scan is a type of scan that combines a series of X-ray images taken from different angles around the body of a patient. Computer processing is used to create cross-sectional images (slices) of the bones, blood vessels, soft tissues, etc. inside of the patient. A non-contrast head CT scan refers to a type of CT scan that focuses on the head (e.g., brain) of the patient, and that is performed without the use of a contrast agent. The non-contrast head CT exam is the initial technique of choice in assessing patients for most acute neurological findings.

SUMMARY

An illustrative system for prioritizing image data includes a memory configured to store image data and metadata corresponding to the image data. The system also includes a processor operatively coupled to the memory and configured to apply a natural language processing algorithm to identify one or more characteristics of the image data and the metadata from the radiology report. The processor is also configured to label the image data based at least in part on the one or more identified characteristics to form a labeled dataset. The processor is further configured to analyze a received image report using the labeled dataset to determine a priority of the received image for the purposes of dataset construction.

In an illustrative embodiment, the metadata comprises textual descriptions of images included in the image report data. In another embodiment, labels of the image data include n-grams associated with the image report data, where the n-grams include unigrams, bigrams, and trigrams. In one embodiment, the one or more identified characteristics include a designation of normal or abnormal. In another embodiment, the one or more identified characteristics include a designation of emergent or non-emergent. In some embodiments, the processor uses a logistic regression model to label the image report data. In another embodiment, the processor is configured to train the logistic regression model with a combination of L2 regularization and five-fold cross validation. In one embodiment, analysis of the received image report comprises a comparison of the received image report to the labeled dataset. The comparison of the received image report to the labeled dataset can include determination of a characteristic that corresponds to the received image report.

An illustrative method for prioritizing image data includes storing, in a memory, image report data and metadata corresponding to the image report data. The method also includes applying, by a processor operatively coupled to the memory, a natural language processing algorithm to identify one or more characteristics of the image report data and the metadata. The method also includes labelling, by the processor, the image report data based at least in part on the one or more identified characteristics to form a labeled dataset. The method further includes analyzing, by the processor, a received image report using the labeled dataset to determine a priority of the received image report.

In an illustrative embodiment, the metadata comprises textual descriptions of images included in the image report data. In one embodiment, the labelling of the image data comprises assigning n-grams associated with images in the image report data, where the n-grams include unigrams, bigrams, and trigrams. In some embodiments, the one or more identified characteristics include a designation of normal or abnormal. In other embodiments, the one or more identified characteristics include a designation of emergent or non-emergent. In one embodiment, the labelling includes using a logistic regression model to label the image report data. In another embodiment, the method can further include training, by the processor, the logistic regression model with a combination of L2 regularization and five-fold cross validation. In another embodiment, analyzing the received image report includes comparing the received image report to the labeled dataset, where the comparison of the received image report to the labeled dataset includes determining a characteristic that corresponds to the received image report.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 1 is a table that depicts in-depth labeling information in accordance with an illustrative embodiment.

DETAILED DESCRIPTION

When conducting a non-contrast head CT exam using traditional systems, the presence of any critical findings is not known at the time of scanning. As a result, patients without sufficient symptoms are often forced to wait several hours before a result is available. During this waiting period, the condition of the patient may deteriorate and/or the opportunity for optimal treatment may close. To help address this unmet clinical need to provide more rapid test results, described herein is a rapid labeling system used to determine the ground truth of a large number of radiology reports, which is used to train and test a machine learning model to automatically detect head CT emergencies and prioritize the reading of CT scans with a strong likelihood of having emergent findings.

Deep learning models have demonstrated broad success on medical image classification tasks. For example, deep learning models can be trained to recognize acute hemorrhages in non-contrast head CTs. A priority system for identifying intracranial hemorrhage has been implemented based on an automated screening algorithm, and the priority system has demonstrated that reading wait times for hemorrhage-positive scans can be reduced without significantly affecting overall turnaround time. These successes indicate the potential feasibility and clinical value of prioritization systems for reading head CT exams. Described herein are algorithms that recognize a plurality of neurological emergencies in radiology reports, which support training of subsequent algorithms not described here which recognize the same plurality of neurological emergencies in images.

Although deep learning methods can deliver the high performance needed for a robust screening system, they require vast amounts of labeled data for training. Manual dataset labelling places an excessive burden on clinical and research staff, raising the need for another approach. Alternatively, the content of clinical radiology reports can be parsed and quantitatively summarized using natural language processing (NLP) algorithms. Rule-based approaches are a class of NLP algorithms where a group of domain experts generate a set of classification rules. This approach can be applied to identify intracranial hemorrhage, fracture, midline shift, and mass effect in head CT reports. Although rules-based approaches can be effective, they involve significant effort from domain experts to create or modify and may have difficulty generalizing beyond the training dataset. Instead, classifier-based approaches for labeling radiology reports can be developed using a training dataset. This approach can additionally be used for detecting fracture, hemorrhage, or stroke in head CT reports.

Initial attempts at creating algorithms that detect critical findings have demonstrated that this is a challenging problem (model accuracy=0.55), and progress may be limited by dataset labeling (NLP labeling accuracy=0.71). The application of higher-performing NLP models, such as those described herein, helps refine datasets for training deep learning algorithms to screen head CT images. Specifically, described herein is a series of NLP models for labelling non-contrast head CT images using the corresponding clinical radiology reports. The dataset labeling approaches described herein can be used to train more advanced head CT prioritization systems, which may ultimately reduce time-to-treatment for patients with acute neurological findings.

An ultimate goal of the proposed system is to automatically detect any of a number (e.g., 21) of critical findings, including intracranial hemorrhage, on head CT exams obtained without intravenous (IV) contrast. This can be done through i) data collection to identify a large dataset of head CT exams and corresponding radiology reports, ii) data labeling to apply natural language processing (NLP) algorithms to identify normal (no significant pathology) vs. abnormal and emergent (no critical pathology) vs. nonemergent exams.

The proposed system was developed based on studies and analyses performed on existing patient data. In one study, 1002 clinical radiology reports from non-contrast head CTs collected between 2008 and 2013 were manually labelled across twelve common neuroradiological finding categories. Each report was then encoded using an n-gram model of unigrams, bigrams, and trigrams. A logistic regression model was then trained to label each report for every common finding. Models were trained and assessed using a combination of L2 regularization and five-fold cross validation.

Referring to the conducted study, radiology reports (97, 553) for non-contrast head CTs performed in the Chicago metropolitan area between 2008 and 2013 were identified through an institutional data warehouse. All subjects were between the ages of 18 and 89, and no subjects were known to be pregnant at the time of scanning. If multiple reports were created for an exam, only the most updated report was kept, and any ambiguities in reporting were clarified by reviewing the corresponding exam.

From the initial search, 1002 reports were randomly selected for manual labeling. This sample size was chosen so that common findings have a reasonable number of positive examples in the dataset for training logistic regression. All sampled reports were included in subsequent analyses. Labeling for all findings was confirmed by a practicing, board-certified neuroradiologist. Each report was labeled across forty-nine finding categories. FIG. 1 is a table that depicts in-depth labeling information in accordance with an illustrative embodiment. The left column of FIG. 1 includes a list of findings for which all 1002 reports were manually labeled. These findings include epidural hemorrhage, subdural hemorrhage, subarachnoid hemorrhage, intra-axial or parenchymal hemorrhage, post-surgical hemorrhage, arterial ischemic infarct, hyperdense artery, acute venous infarct, dural venous sinus thrombosis, subdural fluid collection, subfalcine herniation or midline shift, transtentorial herniation, tonsillar herniation, uncal herniation, craniotomy or craniectomy, upward herniation, significant mass effect or effacement, small mass effect or effacement, ventricular entrapment, postsurgical image, chronic fracture, old aneurysm or arteriovenous malformation, intracranial hypotension, arachnoid cyst, other chronic condition, hemorrhagic transformation of infarct, hydrocephalus, abscess, meningitis, ventriculitis, encephalitis, parenchymal tumor, extra-axial tumor, osseous tumor, metastasis, orbital mass, skull base lysis, white matter disease, acute orbital pathology, fracture, traumatic encephalomalacia, vasogenic edema, cerebral edema, pneumocephalus, chronic white matter disease, chronically prominent ventricles, volume loss, and wallerian degeneration. In alternative embodiments, fewer, additional, and/or different findings may be labeled.

The center column of FIG. 1 includes a corresponding common finding category into which each finding was placed for classification, such as hemorrhage, infarct, herniation, postsurgical, mass effect, hydrocephalus, pneumocephalus, white matter disease, volume loss, etc. If the finding was not grouped into one of the common finding categories, this column reads "Other." In alternative embodiments, fewer, additional, and/or different common finding categories may be used. The right column of FIG. 1 includes the number of reports found with each finding. These finding frequencies formed the basis for clustering of individual findings into common finding categories. It is noted that each report could fall into one, none, or many individual finding or common finding categories.

In addition to labeling across the forty-nine finding categories, the findings were further grouped by disease classes, in order to concatenate report categories with shared language for automated labeling. Finding classes with at least 5% data frequency were kept for further analysis: edema, fracture, hemorrhage, herniation, hydrocephalus, infarct, mass effect, tumor, chronic white matter disease (abbreviated: white matter), pneumocephalus, postsurgical status, and volume loss. This approach ensures that each subsequent finding model has at least fifty positive examples for training. Together, these classes create a comprehensive set of common head CT findings which may summarize the exam reading priority for a majority of patients.

The n-gram model is a technique for encoding text as a sequence of character or word symbols. The modelling approach used for the present system was to encode head CT reports into a vector of word n-gram counts (bag of n-grams) and independently train a logistic regression classifier for each finding type. N-grams were selected because neuroradiologists often repeat concise phrases across reports with specific meaning to imaging findings (e.g., no acute intracranial hemorrhage). N-grams are particularly sensitive to these phrases and are a simple but powerful encoding technique for summarizing document content. Simple models which combine n-grams and logistic regression classifiers have shown strong performance on radiology report labeling. The N-gram counts were not scaled by document length (to n-gram frequency) as the language used to describe abnormal findings is typically longer than the language used to describe normal findings, and adjusting for document length may attenuate this signal. The entire report was used for training as no reliable method was found for segmenting reports into subsections. No stop words were removed as common stop words (i.e., "no", "or", "and") are repeated in key phrases across reports, and these phrases carry important diagnostic value. All reports were split into tokens of consecutive alphanumeric characters, and then the number of unigrams, bigrams, and trigrams were counted using a Natural Language Toolkit (NLTK) library. In alternative embodiments, different operations and/or a different natural language library may be used.

One logistic regression classifier was trained for each of the twelve common findings. Logistic regression classifiers were chosen because of their robust performance, ease of interpretability, straightforward training, and tolerance to class imbalance. Models were trained using a combination of unigrams, bigrams, and trigrams. It was found during training that increasing the gram length improved model performance, and saturated once quadgrams were added. This indicates that the additional feature space provided by quadgrams does not clearly improve linear separability, so n-grams of higher order than trigrams were excluded. Training was performed using L2 regularization, which limits coefficient magnitude and limits model overinterpretation of any single n-gram. Hyperparameter tuning was performed iteratively by setting the L2 coefficient to unity and then adjusting by a factor of 10 until locally maximal performance was realized. All models were trained using the package scikit-learn. In alternative embodiments, different techniques may be used for the training.

Model performance was estimated by averaging the model accuracy, sensitivity, specificity, and area under the receiver-operator characteristic curve (ROC-AUC) across five-fold cross-validation. Reported performance statistics correspond to the point on the ROC curve which maximizes the Dice coefficient (F1-measure), defined as the harmonic mean of the positive predictive value and specificity. This ensures the reported results are not heavily skewed towards predicting the majority class. Each model was then compared to chance using Fisher's exact test for two-way tables.

Across all 97,374 reports which met the study criteria, the average patient age was 53.65+22.24 years (mean+median absolute deviation), and patients were 51.6% female. As compared to a manually labeled cohort of 1002 randomly sampled reports, no significant difference was found between the cohorts in either age (53.54+22.24 years, p=0.81 Wilcoxon Rank Sum Test) or sex (49.9% female, p=0.30 Binomial Test). Expert labeling identified 223 normal reports (22.3%) and 779 reports with at least one abnormality (77.7%). Reports with at least one abnormality described on average 2.44 of the twelve common findings. Furthermore, 97.8% of abnormal reports described at least one of the twelve common findings. All subsequent analyses were performed only on the expert-labeled dataset of 1002 non-contrast head CT reports.

Figure 2:
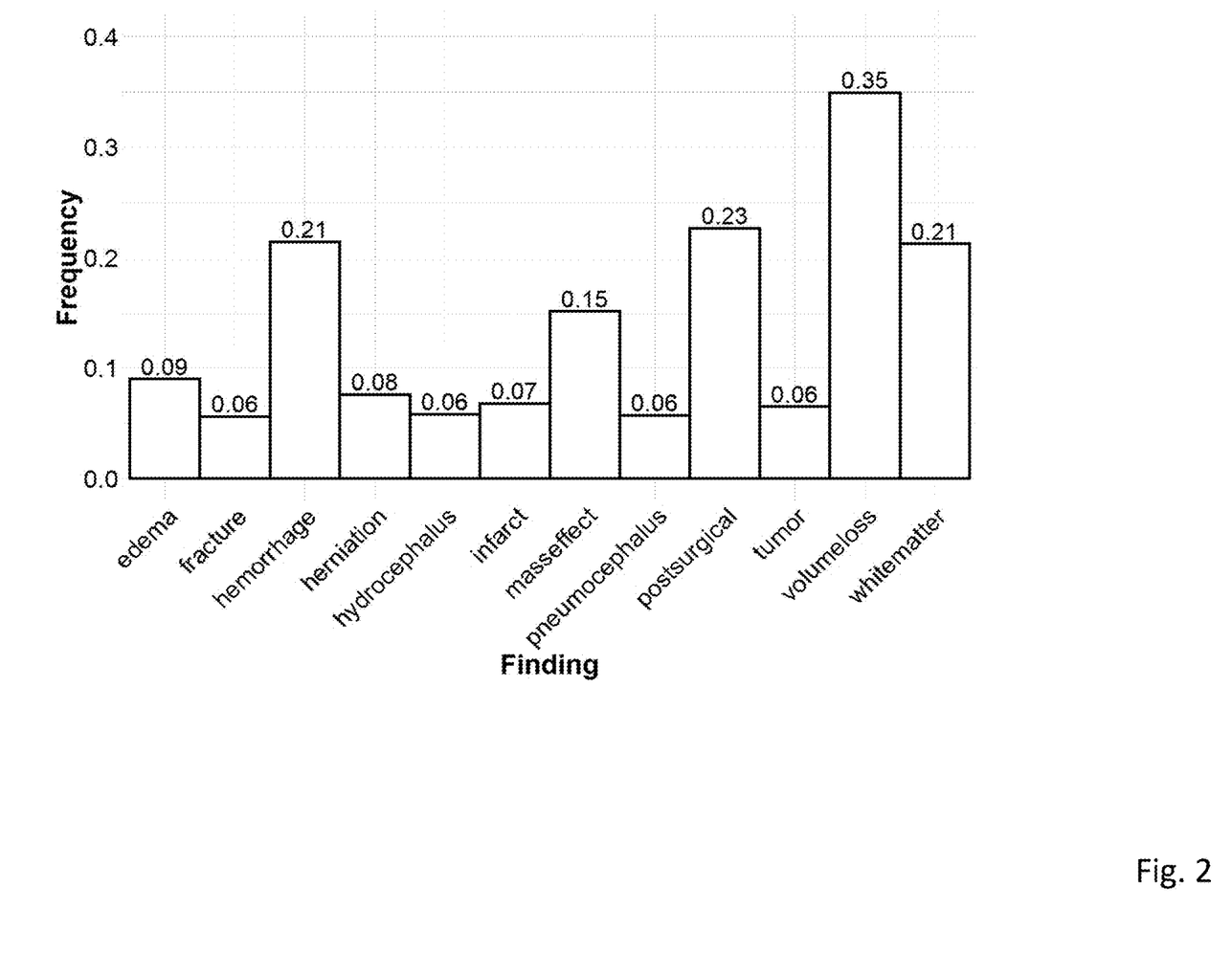
FIG. 2 depicts the frequencies of all twelve common findings in accordance with an illustrative embodiment.

FIG. 2 depicts the frequencies of all twelve common findings in accordance with an illustrative embodiment. Specifically, in FIG. 2, bar lengths and numerical labels represent the frequency of each individual common finding across the labelled radiology reports. It is noted that each report may describe multiple findings, or no findings at all. Volume loss was the most frequent finding overall, described in just over one third of all reports. The next most common findings were postsurgical status (23%), hemorrhage (21%), chronic white matter disease (21%), and mass effect (15%). The remaining findings were overall comparatively rare, occurring at a rate slightly above the inclusion threshold of 5% frequency for common findings. The twelve common findings listed in FIG. 2 include edema, fracture, hemorrhage, herniation, hydrocephalus, infarct, mass effect, pneumocephalus, postsurgical, tumor, volume loss, and white matter. In alternative embodiments, fewer, additional, and/or different common findings may be used for classification.

Figure 3:
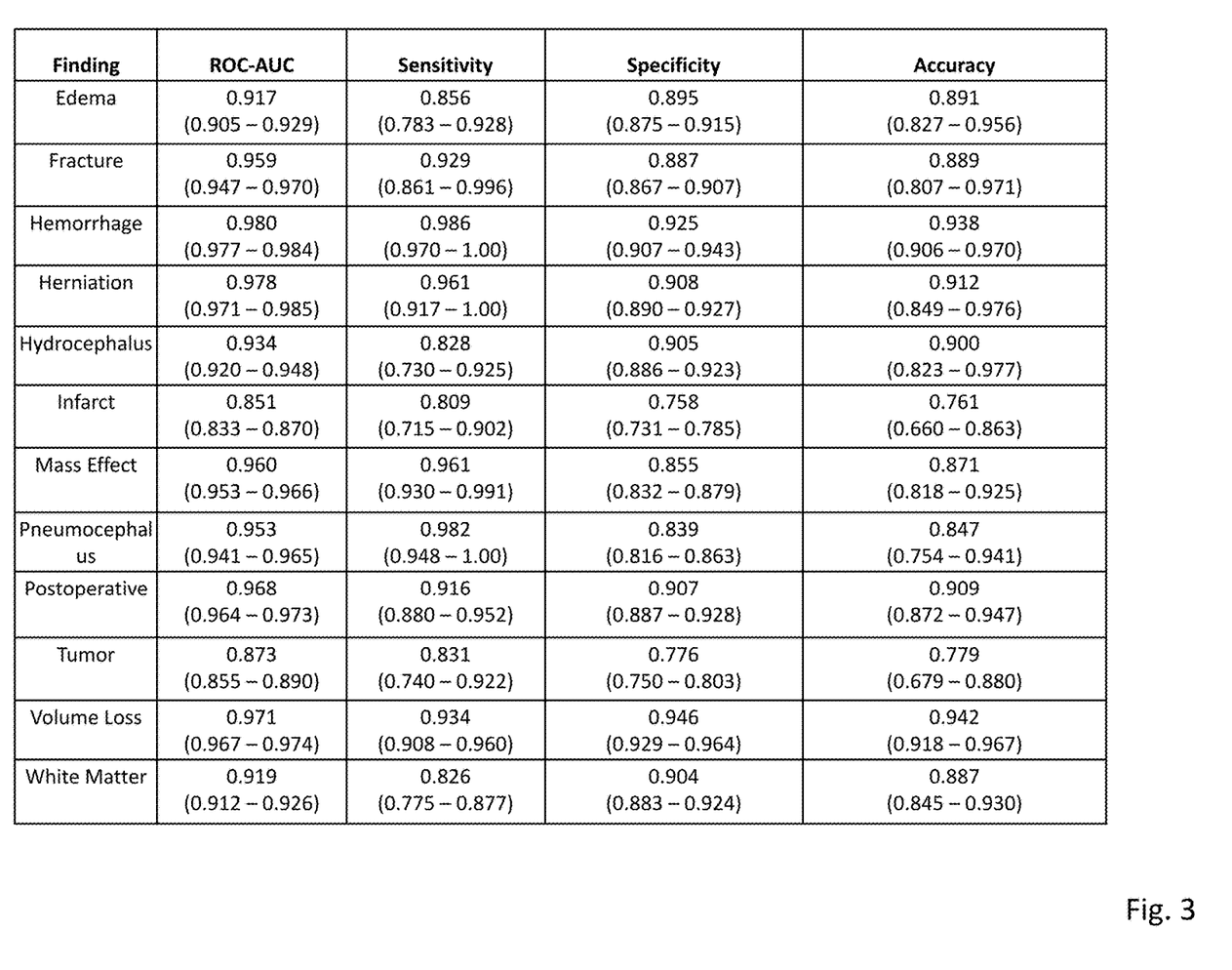
FIG. 3 is a table that depicts the performance for each model in accordance with an illustrative embodiment.

FIG. 3 is a table that depicts the performance for each model in accordance with an illustrative embodiment. In FIG. 3, sensitivities, specificities, accuracies, and area under the receiver-operator characteristic curve (ROC-AUC) are shown for each finding model. Additionally, 95% confidence intervals are displayed for each metric. All performance metrics were measured using five-fold cross-validation. Models for detecting infarct and tumors were the weakest by all metrics. Sensitivity and specificity were relatively close (within 5%) for the edema, fracture, postoperative, and volume loss models. Sensitivity was considerably higher than specificity for the hemorrhage, herniation, infarct, mass effect, pneumocephalus, and tumor models. Only the model for white matter disease had considerably lower sensitivity than specificity. As discussed in more detail below, it was found that each model performed the respective binary classification task significantly better than chance (Fisher's exact test for two-way tables, p<0.001).

Figure 4A:
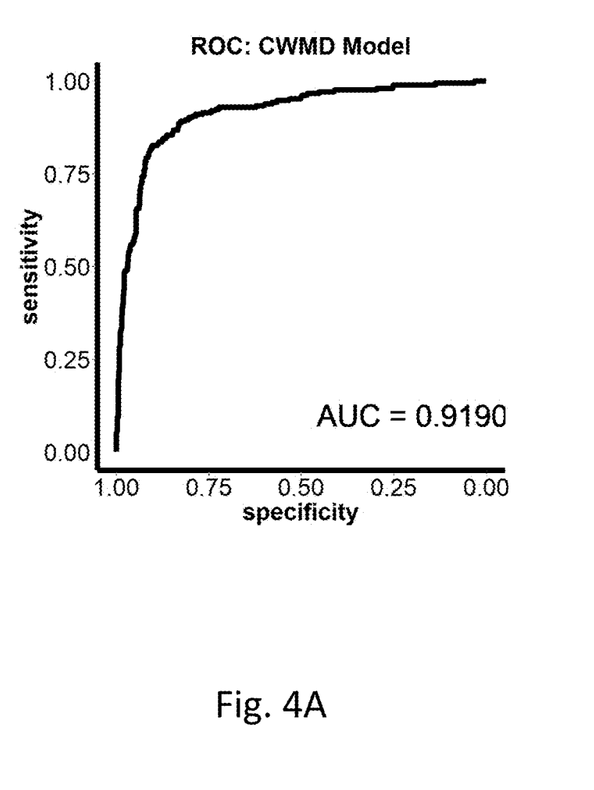
FIG. 4A is an ROC curve for a CWMD model in accordance with an illustrative embodiment.
Figure 4B:
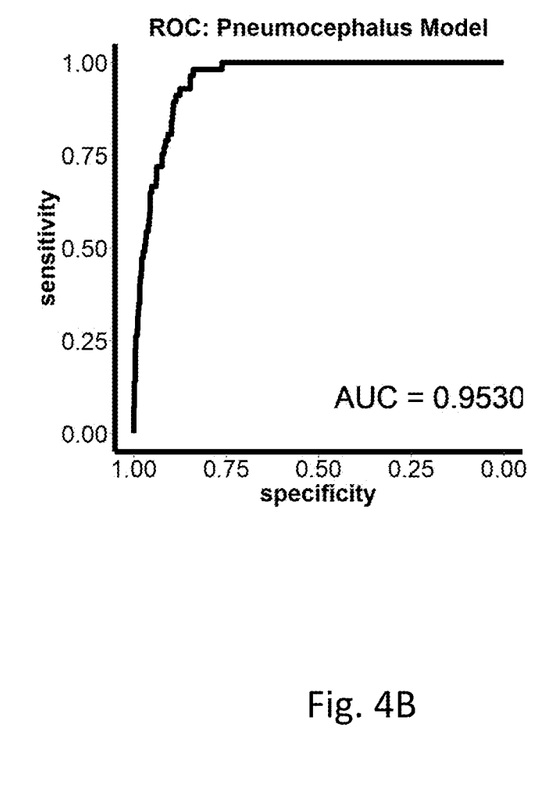
FIG. 4B is an ROC curve for a pneumocephalus model in accordance with an illustrative embodiment.
Figure 4C:
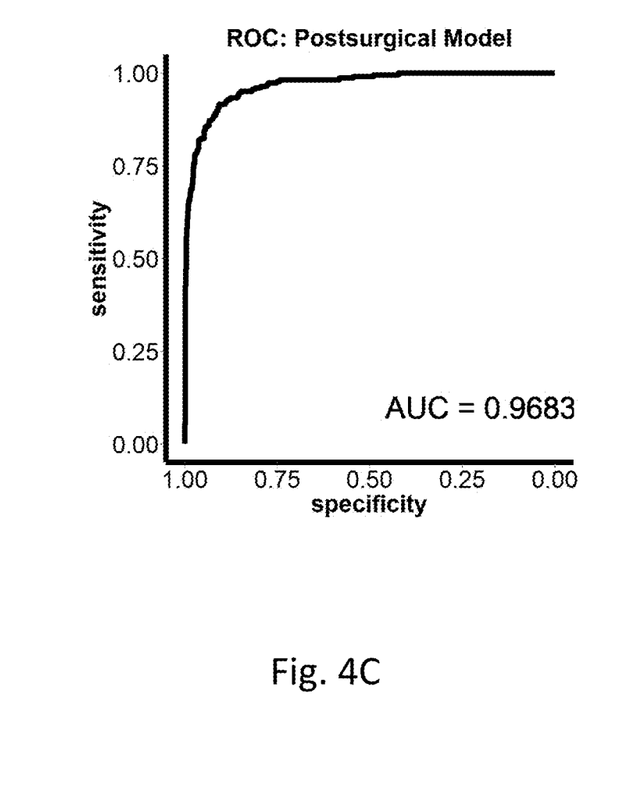
FIG. 4C is an ROC curve for a postsurgical model in accordance with an illustrative embodiment.
Figure 4D:
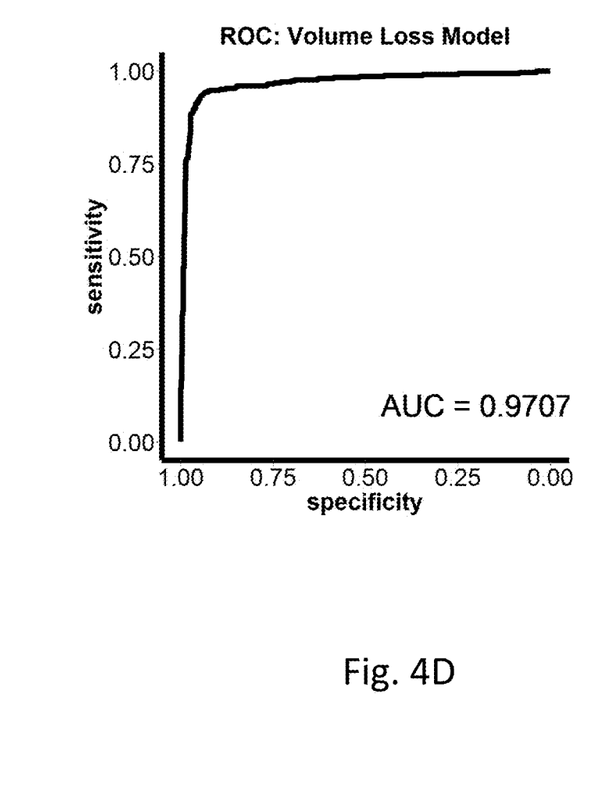
FIG. 4D is an ROC curve for a volume loss model in accordance with an illustrative embodiment.
Figure 4E:
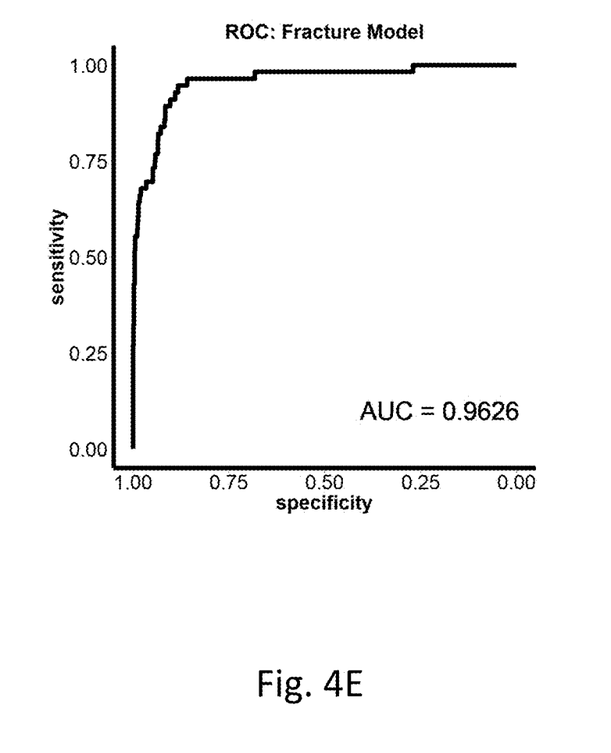
FIG. 4E is an ROC curve for a fracture model in accordance with an illustrative embodiment.
Figure 4F:
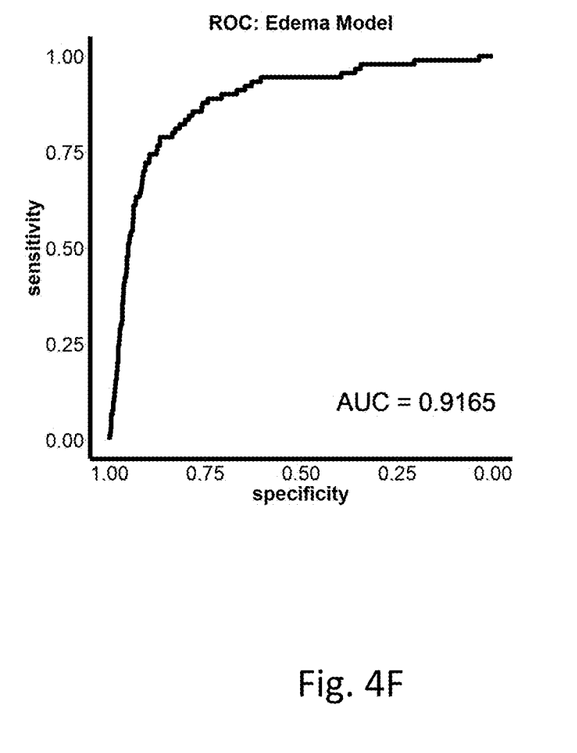
FIG. 4F is an ROC curve for an edema model in accordance with an illustrative embodiment.
Figure 4G:
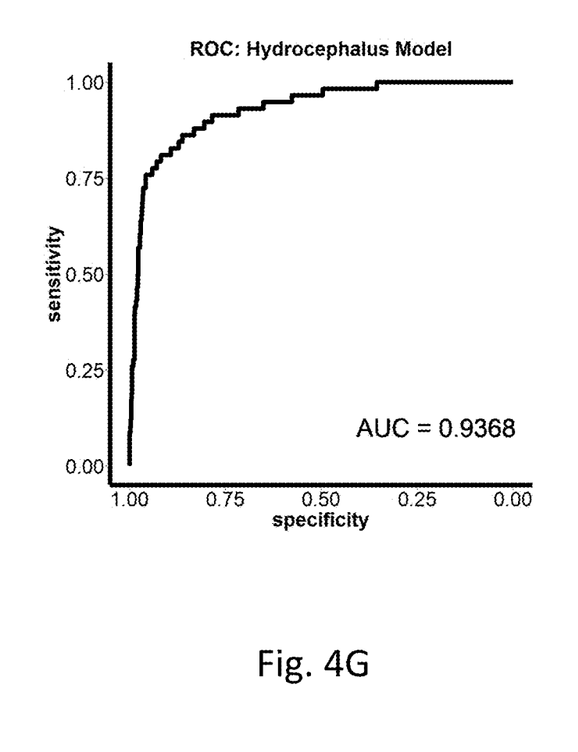
FIG. 4G is an ROC curve for a hydrocephalus model in accordance with an illustrative embodiment.
Figure 4H:
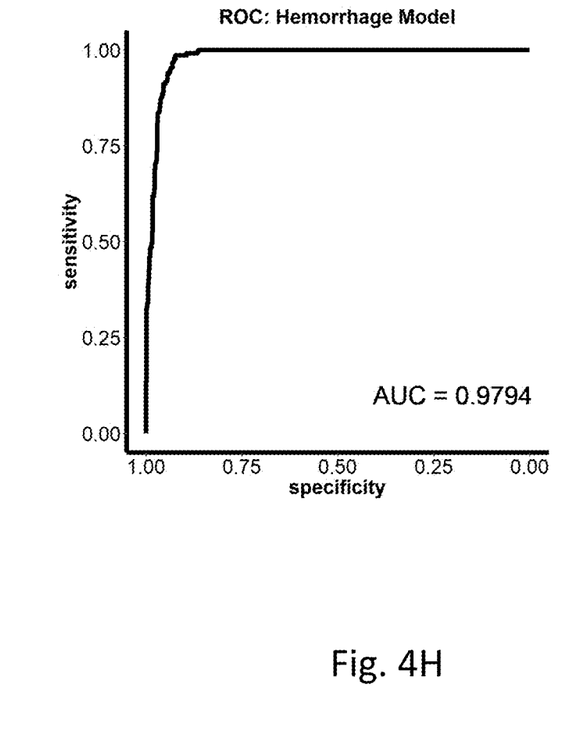
FIG. 4H is an ROC curve for a hemorrhage model in accordance with an illustrative embodiment.
Figure 4I:
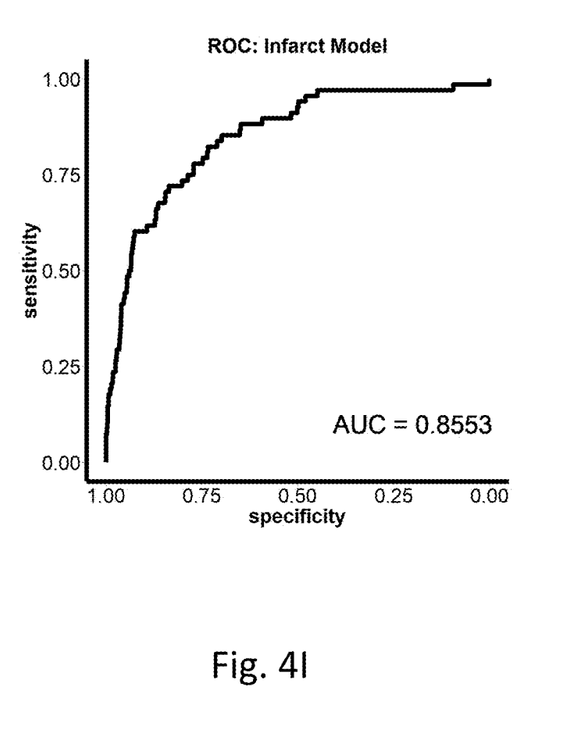
FIG. 4I is an ROC curve for an infarct model in accordance with an illustrative embodiment.
Figure 4J:
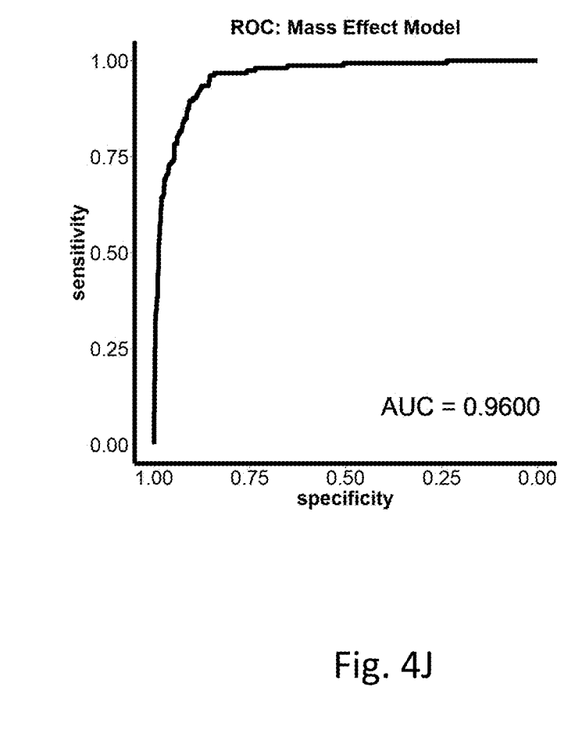
FIG. 4J is an ROC curve for a mass effect model in accordance with an illustrative embodiment.
Figure 4K:
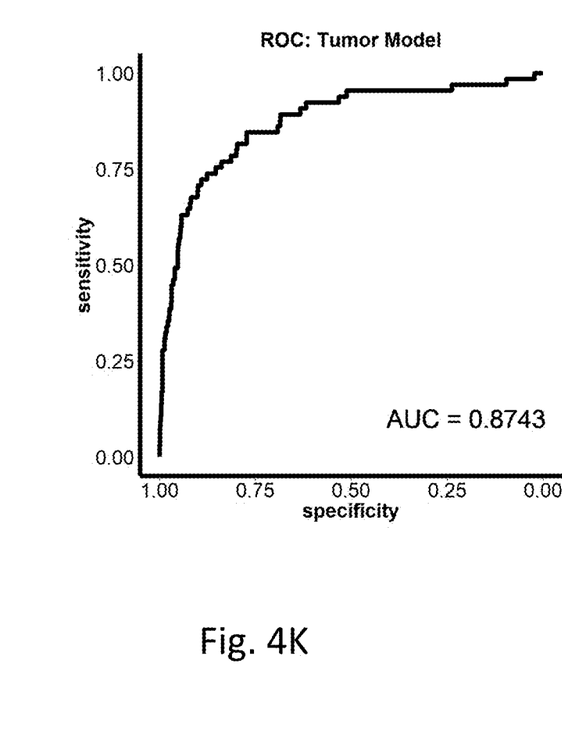
FIG. 4K is an ROC curve for a tumor model in accordance with an illustrative embodiment.
Figure 4L:
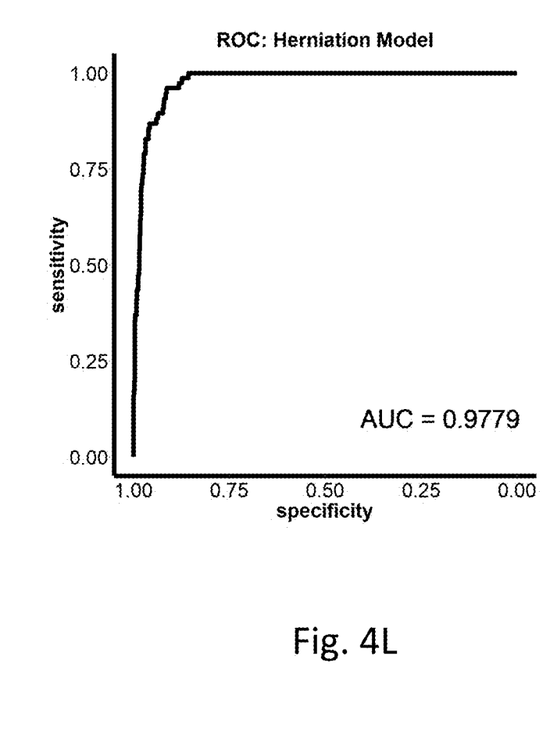
FIG. 4L is an ROC curve for a herniation model in accordance with an illustrative embodiment.

Based on the ROC-AUC, the models for hemorrhage, herniation, and volume loss performed best (ROC-AUC>0.97), closely followed by those for postoperative status, fracture, mass effect, and pneumocephalus (ROC-AUC>0.95). FIG. 4 depicts ROC curves for each model in accordance with an illustrative embodiment. Specifically, FIG. 4A is an ROC curve for a chronic white matter disease (CWMD) model in accordance with an illustrative embodiment. FIG. 4B is an ROC curve for a pneumocephalus model in accordance with an illustrative embodiment. FIG. 4C is an ROC curve for a postsurgical model in accordance with an illustrative embodiment. FIG. 4D is an ROC curve for a volume loss model in accordance with an illustrative embodiment. FIG. 4E is an ROC curve for a fracture model in accordance with an illustrative embodiment. FIG. 4F is an ROC curve for an edema model in accordance with an illustrative embodiment. FIG. 4G is an ROC curve for a hydrocephalus model in accordance with an illustrative embodiment. FIG. 4H is an ROC curve for a hemorrhage model in accordance with an illustrative embodiment. FIG. 4I is an ROC curve for an infarct model in accordance with an illustrative embodiment. FIG. 4J is an ROC curve for a mass effect model in accordance with an illustrative embodiment. FIG. 4K is an ROC curve for a tumor model in accordance with an illustrative embodiment. FIG. 4L is an ROC curve for a herniation model in accordance with an illustrative embodiment.

Figure 5:
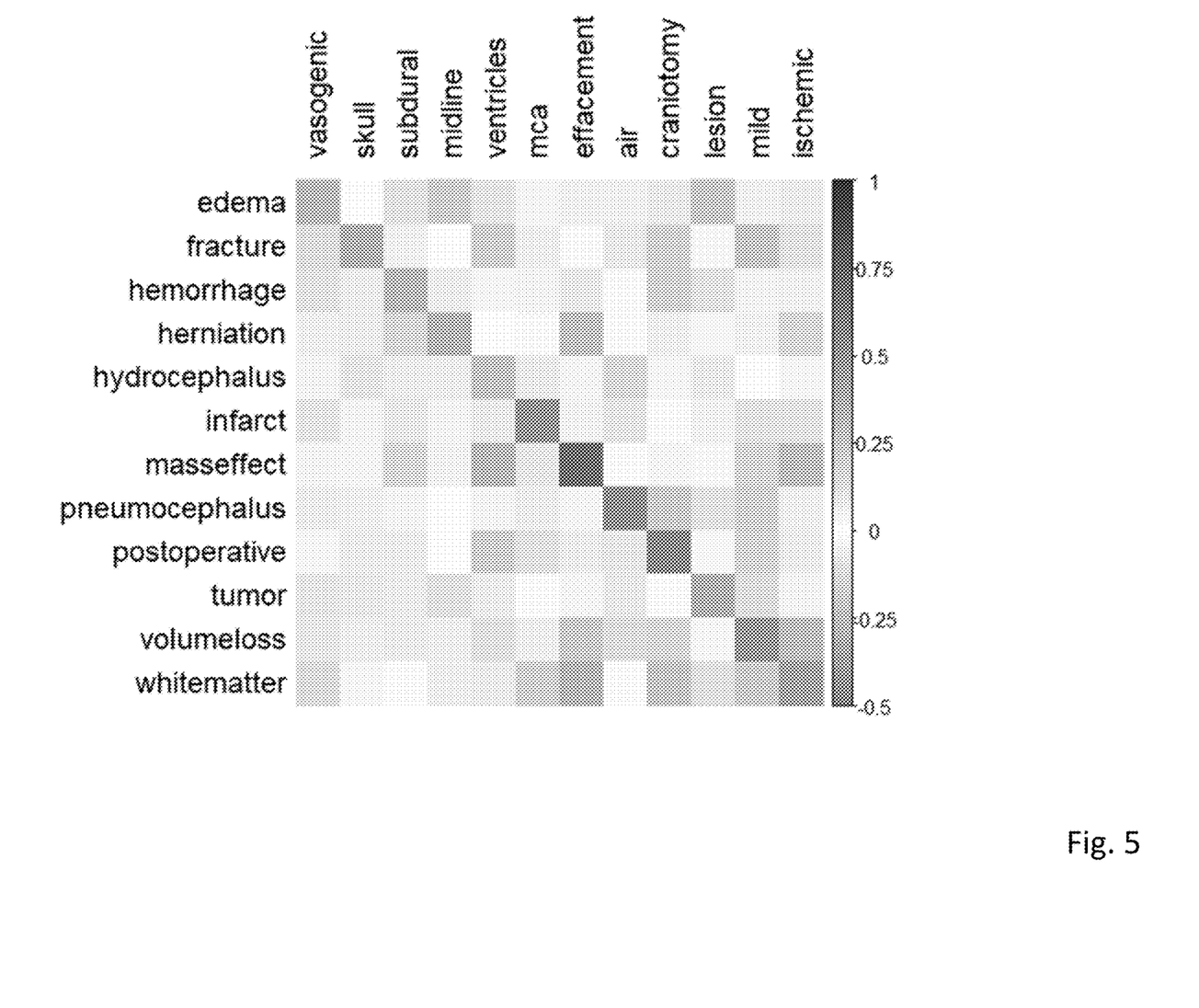
FIG. 5 is a heatmap of selected model coefficients in accordance with an illustrative embodiment.

FIG. 5 is a heatmap of selected model coefficients in accordance with an illustrative embodiment. Normalized model coefficients corresponding to selected unigrams (horizontal axis labels) are shown for each model (vertical axis labels). Lighter values indicate positive association between unigram frequency and probability of the corresponding finding. One unigram was chosen from a list of five n-grams with largest coefficients in each model. Coefficient labels are ordered by model of origin ("vasogenic" is the selected unigram for the edema model, "skull" is the selected unigram for the fracture model, etc.). Preference was given to n-grams which were closely related to the finding of interest. N-grams which contained the finding word or words were not chosen for display, although these were typically the n-grams with highest coefficients in each model. Coefficients were normalized by row and column averages for better comparison across models, as coefficients are strongly affected by the n-gram frequency and model regularization terms.

All models had unigrams which closely relate to the finding pathology or description within the top five coefficients. For most models, the largest coefficients were either unigrams or combinations of those same unigrams. For example, the terms "edema", "vasogenic", and "vasogenic edema" were among the highest for the edema model. N-grams with the most negative coefficients were generally lower in magnitude than n-grams with the most positive coefficients, and were typically nonspecific or negatory (i.e. "no acute intracranial" was a strongly negative trigram for the hemorrhage model). Selected coefficients had higher magnitude for their corresponding model than for other models (visible through the diagonal line), suggesting that each model identified important n-grams that were unique to the specific finding.

It is known that training machine learning algorithms to screen head CT images for emergent findings can be hindered by inaccurate labeling. Although model training is typically performed using binary labels, most machine learning algorithms output class probabilities which are thresholded to determine the binary class label. Training protocols that take into account class output probabilities instead of only binary labels are a possible solution to overcome the noisy labeling problem. In order to better understand the validity of class output probabilities in the models, the inventors iteratively removed data points closest to the decision boundary (i.e., least certain predictions) and observed the change in overall error rate.

Figure 6:
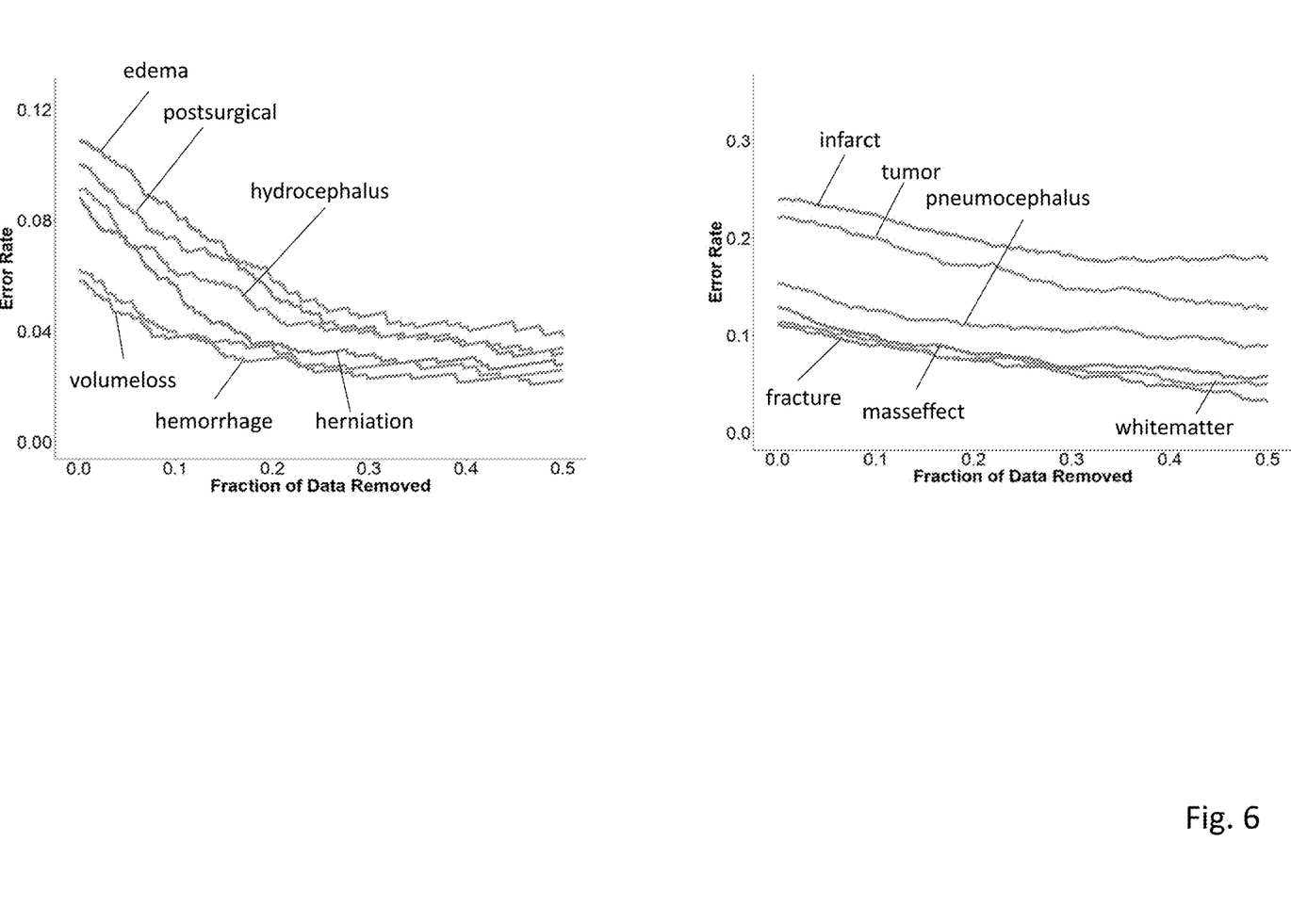
FIG. 6 depicts visualizing model discrimination by filtering uncertain predictions in accordance with an illustrative embodiment.

FIG. 6 depicts visualizing model discrimination by filtering uncertain predictions in accordance with an illustrative embodiment. Changes in error rate are shown for higher performing models (left) and lower performing models (right) when data near the decision boundary are removed. Error rate is calculated as one minus the model accuracy. It was found that error rate decreases for all models when uncertain predictions are removed, indicating that correct predictions are overall classified more confidently than incorrect ones. This effect is magnified for models with higher initial performance, where the error rate tends to decrease approximately exponentially when data are removed, whereas the error rate of models with lower initial performance decreases linearly.

A series of NLP models were used for labeling non-contrast head CT images using the corresponding radiology reports. The overall strong performance of the models suggests that the combination of n-grams and logistic regression is suitable for labeling common findings in head CT reports (FIG. 2, ROC-AUC: 0.851-0.980, Accuracy: 0.761-0.942). While other higher-order models were experimented with during the model selection process, including random forests and neural networks, logistic regression models were found to be the most consistent. This is because linear models have fewer parameters than more complex, nonlinear models and are easier to train with lower amounts of labeled data. Furthermore, the addition of bigrams and trigrams in the input vector creates a higher complexity feature space in which the task of labeling common findings is closer to being linearly separable.

An additional benefit of using logistic regression over more complex models is ease of interpretability. Each of the models used identified specific words which align with the anatomical features for each finding. This suggests that the model is engaging with the common neuroradiological vocabulary as opposed to noisy higher-order features, and is promising for generalization to other datasets. Furthermore, logistic regression models provide a class output probability which can serve as a measure of prediction confidence. In the stronger models, this probability was indicative of the error rate for each report, enabling lowering of the error rate by removing less certain predictions. While this decreases the labeled dataset size, there is currently a surplus of unlabeled radiology reports. The benefits of a less noisy training dataset outweigh the cost of lower sample size in training machine learning models to identify findings in head CT images, provided that removal of these data points does not create a non-representative training dataset.

When compared to a prior study, the proposed techniques developed comparatively strong models for identifying fractures (ROC-AUC: 0.959 vs 0.816-0.930) and hemorrhage (ROC-AUC: 0.980 vs. 0.918-0.945). These improvements over prior techniques are due to several methodological differences. First, cross-validation was used instead of a large hold-out group for model testing, which allows training on the entire dataset without compromising estimation of model performance. Second, stop words were not filtered, which may have preserved more information in the training dataset. Additionally, Ridge (L2) regularization was applied as opposed to LASSO (L1) regularization. Although sparse weighting of variables may improve generalization in some datasets, head CT reports are composed of many highly correlated n-gram features which compete for coefficient magnitude under LASSO regularization. Ridge regularization instead distributes coefficient magnitude across correlated features which better handles variance in expression across reports.

To summarize the analyses, it was found that all models labeled reports for common findings at a rate better than chance (Fisher's exact test, p<<0.01). Performance was strongest for the fracture, hemorrhage, herniation, mass effect, pneumocephalus, postoperative status, and volume loss models, where the area under the receiver-operator characteristic curve (ROC-AUC) exceeded 0.95. Performance was weaker for the edema, hydrocephalus, infarct, tumor, and white-matter disease models (ROC-AUC>0.85). Analysis of coefficients revealed finding-specific words among the top coefficients in each model, and class output probabilities were found to be a useful indicator of predictive error on individual report examples in higher-performing models.

Thus, in addition to presenting models for labeling reports, described herein is a twelve-dimensional framework for common head CT findings. Although this framework is straightforward, it is a practical step towards a next-generation head CT screening system. Assigning head CT exams a meaningful priority score involves interpretation of finding interaction effects. For example, a tumor which also presents with edema and mass effect is more severe than one that does not. Alternatively, the presence of pneumocephalus in a postsurgical patient is often expected, while an isolated pneumocephalus may have a more insidious cause and warrants higher priority. This twelve-finding framework allows for interpreting multiplicative relationships between findings on exam priority, while also improving model training by lowering the problem dimensionality. Combining logistic regression with n-gram encoding is therefore a robust approach to labeling common findings in non-contrast head CT reports.

Figure 7:
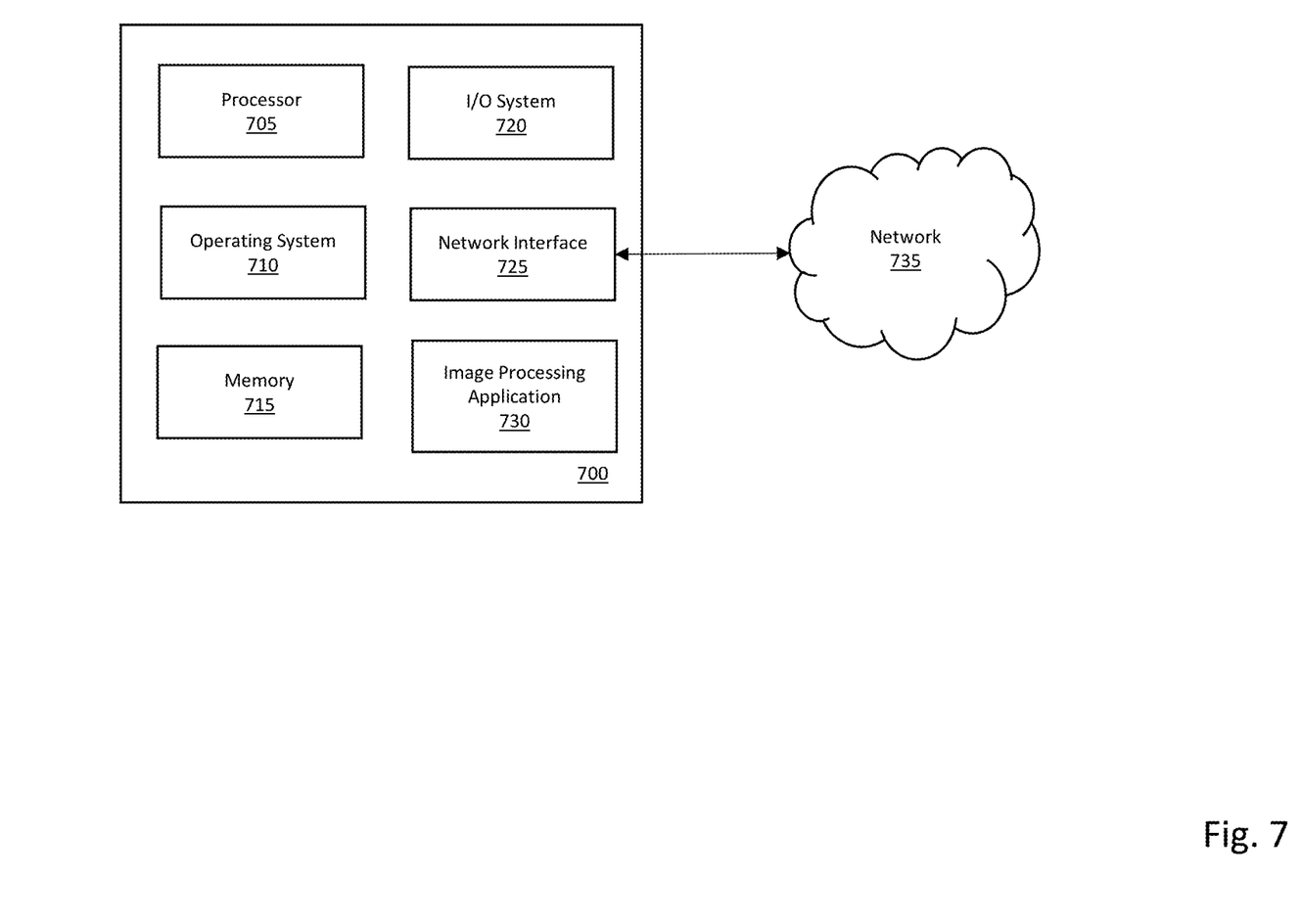
FIG. 7 depicts a computing system in direct or indirect communication with a network in accordance with an illustrative embodiment.

In an illustrative embodiment, prioritized reading of non-contrast head CT exams can be performed through an automated triage computing system to improve time-to-care for patients with acute neuroradiologic findings. The computing system can facilitate a natural language processing approach for labeling findings in non-contrast head CT reports, which permits creation of a large, labeled dataset of head CT images for development of emergent finding detection and reading prioritization algorithms. FIG. 7 depicts a computing system 700 in direct or indirect communication with a network 735 in accordance with an illustrative embodiment. The computing system 700 includes a processor 705, an operating system 710, a memory 715, an input/output (I/O) system 720, a network interface 725, and an image processing application 730. In alternative embodiments, the computing system 700 may include fewer, additional, and/or different components. The components of the computing device 700 communicate with one another via one or more buses or any other interconnect system.

The processor 705 of the computing system 700 can be in electrical communication with and used to perform any of the operations described herein, such as gathering data, processing the gathered data, labeling images, analyzing and prioritizing received images, etc. The processor 705 can be any type of computer processor known in the art, and can include a plurality of processors and/or a plurality of processing cores. The processor 705 can include a controller, a microcontroller, an audio processor, a graphics processing unit, a hardware accelerator, a digital signal processor, etc. Additionally, the processor 705 may be implemented as a complex instruction set computer processor, a reduced instruction set computer processor, an x86 instruction set computer processor, etc. The processor 705 is used to run the operating system 710, which can be any type of operating system.

The operating system 710 is stored in the memory 715, which is also used to store programs, image data, labels, algorithms, network and communications data, peripheral component data, and other operating instructions. In an illustrative embodiment, the memory 715 stores computer-readable instructions that can perform any of the operations described herein. The computer-readable instructions can be executed by the processor 705 to perform the operations. The memory 715 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 720, or user interface, is the framework which enables users (and peripheral devices) to interact with the computing system 700. The I/O system 720 can include one or more keys or a keyboard, one or more buttons, one or more displays, a speaker, a microphone, etc. that allow the user to interact with and control the computing system 700. The I/O system 720 also includes circuitry and a bus structure to interface with peripheral computing components such as power sources, sensors, etc.

The network interface 725 includes transceiver circuitry (e.g., one or more transmitters and one or more receivers) that allows the computing system 700 to transmit and receive data to/from other devices such as user device(s), remote computing systems, servers, websites, etc. The network interface 725 enables communication through the network 735, which can be one or more communication networks. The network 735 can include a cable network, a fiber network, a cellular network, a wi-fi network, a landline telephone network, a microwave network, a satellite network, etc. The network interface 725 also includes circuitry to allow device-to-device communication such as near field communication (NFC), Bluetooth® communication, etc.

The image processing application 730 can include hardware, software, and algorithms (e.g., in the form of computer-readable instructions) which, upon activation or execution by the processor 705, performs any of the various operations described herein such as receiving image report data, applying natural language processing algorithms to label the image report data. The image processing application 730 can utilize the processor 705 and/or the memory 715 as discussed above. For example, all or a portion of the image processing application 730 can be stored in the memory 715, and the processor 705 can be used to execute any of the operations stored in the image processing application 730.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A system for labeling massive quantities of image report data, the system comprising:
   a memory configured to store image report data; and
   a processor operatively coupled to the memory and configured to:
   apply a natural language processing algorithm to identify one or more characteristics of the image report, wherein the one or more characteristics include n-grams identified in the image report data;
   identify one or more phrases in the image report data, wherein the one or more phrases are identified based on a model of encodings of the n-grams identified in the image report data;
   label the image report data based at least in part on the one or more identified phrases to form a labeled dataset; and
   analyze a received image report using the labeled dataset to determine a priority of the received image report.

2. The system of claim 1, wherein the image report data includes metadata, and wherein the metadata comprises textual descriptions of images included in the image report data.

3. The system of claim 1, wherein the n-grams include only unigrams, bigrams, and trigrams.

4. The system of claim 1, wherein the one or more identified characteristics include a designation of normal or abnormal.

5. The system of claim 1, wherein the one or more identified characteristics include a designation of emergent or non-emergent.

6. The system of claim 1, wherein the processor uses a logistic regression model to label the image data.

7. The system of claim 6, wherein the processor is configured to train the logistic regression model with a combination of L2 regularization and five-fold cross validation.

8. The system of claim 1, wherein analysis of the received image report comprises a comparison of the received image report to the labeled dataset.

9. The system of claim 8, wherein the comparison of the received image report to the labeled dataset includes determination of a characteristic that corresponds to the received image report.

10. A method for prioritizing images based on their metadata, the method comprising:
    storing, in a memory, image report data;
    applying, by a processor operatively coupled to the memory, a natural language processing algorithm to identify one or more characteristics of the image report data, wherein the one or more characteristics include n-grams identified in the image report data;
    identifying, by the processor, one or more phrases in the image report data, wherein the one or more phrases are identified based on a model of encodings of the n-grams identified in the image report data; and
    labelling, by the processor, the image report data based at least in part on the one or more identified phrases to form a labeled dataset.

11. The method of claim 10, wherein the image report data includes metadata, and wherein the metadata comprises textual descriptions of images included in the image report data.

12. The method of claim 10, wherein the n-grams include only unigrams, bigrams, and trigrams.

13. The method of claim 10, wherein the one or more identified characteristics include a designation of normal or abnormal.

14. The method of claim 10, wherein the one or more identified characteristics include a designation of emergent or non-emergent.

15. The method of claim 10, wherein the labelling includes using a logistic regression model to label the image report data.

16. The method of claim 15, further comprising training, by the processor, the logistic regression model with a combination of L2 regularization and five-fold cross validation.

17. The method of claim 10, further comprising analyzing, by the processor, a received image using the labeled dataset to determine a priority of the received image, wherein the analyzing the received image includes comparing the received image to the labeled dataset.

18. The method of claim 17, wherein the comparison of the received image to the labeled dataset includes determining a characteristic that corresponds to the received image.

* * * * *